(12) United States Patent
Yang et al.

(10) Patent No.: US 6,517,575 B1
(45) Date of Patent: Feb. 11, 2003

(54) MULTILAYER LIQUID ABSORPTION AND DEFORMATION DEVICES

(75) Inventors: Dachuan Yang, Plymouth, MN (US); Lixiao Wang, Maple Grove, MN (US)

(73) Assignee: SciMed Life Systems, Inc., Maple Grove, MN (US)

(*) Notice: Subject to any disclaimer, the term of this patent is extended or adjusted under 35 U.S.C. 154(b) by 0 days.

(21) Appl. No.: 09/609,584

(22) Filed: Jun. 30, 2000

Related U.S. Application Data

(63) Continuation of application No. 08/775,741, filed on Dec. 31, 1996, now Pat. No. 6,117,168.

(51) Int. Cl.⁷ .................................................. A61F 2/06
(52) U.S. Cl. ................. 623/1.44; 623/11.11; 623/23.64
(58) Field of Search ............................ 623/1.44, 11.11, 623/23.64, 23.65, 23.66, 23.69, 23.7, 23.71, 1.2, 1.22, 1.46, 1.47; 606/194, 198, 195; 600/36; 604/264, 265; 428/35.2

(56) References Cited

U.S. PATENT DOCUMENTS

| 4,387,413 A | 6/1983 | Griffis |
| 4,445,105 A | 4/1984 | Wehl |
| 4,460,642 A | 7/1984 | Errede et al. |
| 4,496,535 A | 1/1985 | Gould et al. |
| 4,814,131 A * | 3/1989 | Atlas ........................ 264/147 |
| 4,872,867 A | 10/1989 | Joh |
| 4,994,047 A * | 2/1991 | Walker et al. .............. 604/264 |
| 5,102,401 A | 4/1992 | Lambert et al. ............ 604/264 |
| 5,163,952 A | 11/1992 | Froix |
| 5,234,456 A | 8/1993 | Silvestrini |
| 5,236,447 A * | 8/1993 | Kubo et al. ..................... 623/1 |
| 5,258,020 A | 11/1993 | Froix |
| 5,270,086 A * | 12/1993 | Hamlin ..................... 428/36.92 |
| 5,306,250 A | 4/1994 | March et al. |
| 5,356,423 A | 10/1994 | Tihon et al. |
| 5,389,106 A | 2/1995 | Tower |
| 5,443,458 A | 8/1995 | Eury |
| 5,443,495 A | 8/1995 | Buscemi et al. |
| 5,464,419 A | 11/1995 | Glastra |
| 5,464,450 A | 11/1995 | Buscemi et al. |
| 5,500,013 A | 3/1996 | Buscemi et al. |
| 5,554,180 A | 9/1996 | Turk |
| 5,599,291 A | 2/1997 | Balbierz et al. |
| 5,632,776 A * | 5/1997 | Kurumatani et al. ........... 623/1 |
| 5,674,241 A | 10/1997 | Bley et al. |
| 5,735,897 A | 4/1998 | Buirge |
| 6,117,168 A | 9/2000 | Yang et al. ................ 623/1.44 |
| 6,132,824 A * | 10/2000 | Hamlin ....................... 428/35.2 |

FOREIGN PATENT DOCUMENTS

| EP | 0 502 905 B1 | 6/1991 |
| EP | 0 441 516 B1 | 8/1991 |
| EP | 0 547 530 B1 | 9/1996 |
| JP | 63-97158 A | 4/1988 |
| WO | WO93/10827 | 6/1993 |
| WO | WO95/10989 | 4/1995 |
| WO | WO96/25897 | 8/1996 |

OTHER PUBLICATIONS

Dialog Search Dated Oct. 24, 1996.

* cited by examiner

*Primary Examiner*—David J. Isabella
(74) *Attorney, Agent, or Firm*—Vidas, Arrett & Steinkraus

(57) ABSTRACT

A multilayer device comprised of at least one layer of material which is capable of absorbing liquid to thereby increase the volume of the layer, i.e., liquid swellable, and when bound to at least one non-absorbing or lesser absorbing layer of material causes deformation of the device upon liquid absorption.

16 Claims, 4 Drawing Sheets

MULTILAYER LIQUID ABSORPTION AND DEFORMATION DEVICES

CROSS-REFERENCE TO RELATED APPLICATIONS

This application is a continuation of U.S. patent application Ser. No. 08/775,741 filed Dec. 31, 1996, now U.S. Pat. No. 6,117,168 the contents of which are incorporated herein by reference.

BACKGROUND OF THE INVENTION

This invention relates generally to multilayer liquid absorption and deformation devices. More particularly, it relates to such devices for medical purposes and most particularly it relates to self-expandable intraluminal vascular stents employing such devices wherein the liquid is water.

In some embodiments, the stents may be biodegradable or they may be capable of releasing therapeutic drugs or they may be capable of doing both simultaneously.

Biodegradable and drug releasing stents and other medical devices are not new in the art as evidenced, for example, by the following patents: U.S. Pat. No. 5,306,250 to March et al. on Apr. 26, 1994; U.S. Pat. No. 5,443,458 to Eury et al. on Aug. 22, 1995; U.S. Pat. No. 5,443,495 to Buscemi et al. on Aug. 22, 1995; U.S. Pat. No. 5,464,450 to Buscemi et al. on Nov. 7, 1995; U.S. Pat. No. 5,500,013 to Buscemi et al. on Mar. 19, 1996 and Japanese patent application J63-9715 8 A, published Apr. 27, 1988.

U.S. Pat. No. 5,389,106 to Tower on Feb. 14, 1995 describes a stent having an impermeable polymer membrane disposed inside a wire frame. However, the membrane is not biodegradable.

Devices making use of water swellable material, some of which are stents, are described in U.S. Pat. No. 4,460,642 to Errede et al. on Jul. 17, 1984; U.S. Pat. No. 4,496,535 to Gould et al. on Jan. 29, 1985; U.S. Pat. No. 4,872,867 to Joh on Oct. 10, 1989; U.S. Pat. No. 5,163,952 to Froix on Nov. 17, 1992; U.S. Pat. No. 5,234,456 to Silvestrini on Aug. 10, 1993; U.S. Pat. No. 5,258,020 to Froix on Nov. 2, 1993; U.S. Pat. No. 5,464,419 to Glastra on Nov. 7, 1995; U.S. Pat. No. 5,554,180 to Turk on September 1996; EP patent 0502905B1 on Sep. 14, 1994 and EP patent 0441516B1 on Mar. 29, 1995. None of these patents make use of swellable material in the manner of this invention nor for the same purpose.

The content of all of the above-identified patents are incorporated herein by reference.

SUMMARY OF THE INVENTION

The basic concept of this invention is analogous in a general way to a bimetal. A bimetal comprises two metals bonded together that expand differently to undergo deflection. For example, the best known bimetal may be the type consisting of two thin strips of metal having different thermal expansion coefficients bonded together. Deflection or bending of such a structure is in response to temperature change. Such bimetals in the form of a beam, helical or spiral structure have been commonly used in temperature sensing devices such as thermostats and thermometers.

This invention on the other hand and in an analogous way combines two or more layers of material together in superimposed fashion in which at least two of the layers exhibit differential liquid absorbency. For example, a two layer structure in which one layer is hydrophilic and the other layer is not or which is less hydrophilic than the one layer will, upon exposure to water, analogously undergo deflection or bending because the absorption of water by the hydrophilic layer causes swelling of the layer. Since it is superimposed upon the other layer, deflection or bending results in a way analogous to the deflection of bimetal structures already described.

A beam-like structure may be used as an actuator or the like to respond or signify the presence of water or some other absorbable liquid.

The concept, as will be described in further detail hereinbelow, may be used in a variety of medical applications although not limited thereto, including self-expanding stents.

DETAILED DESCRIPTION OF THE PREFERRED EMBODIMENTS

Figure 1:
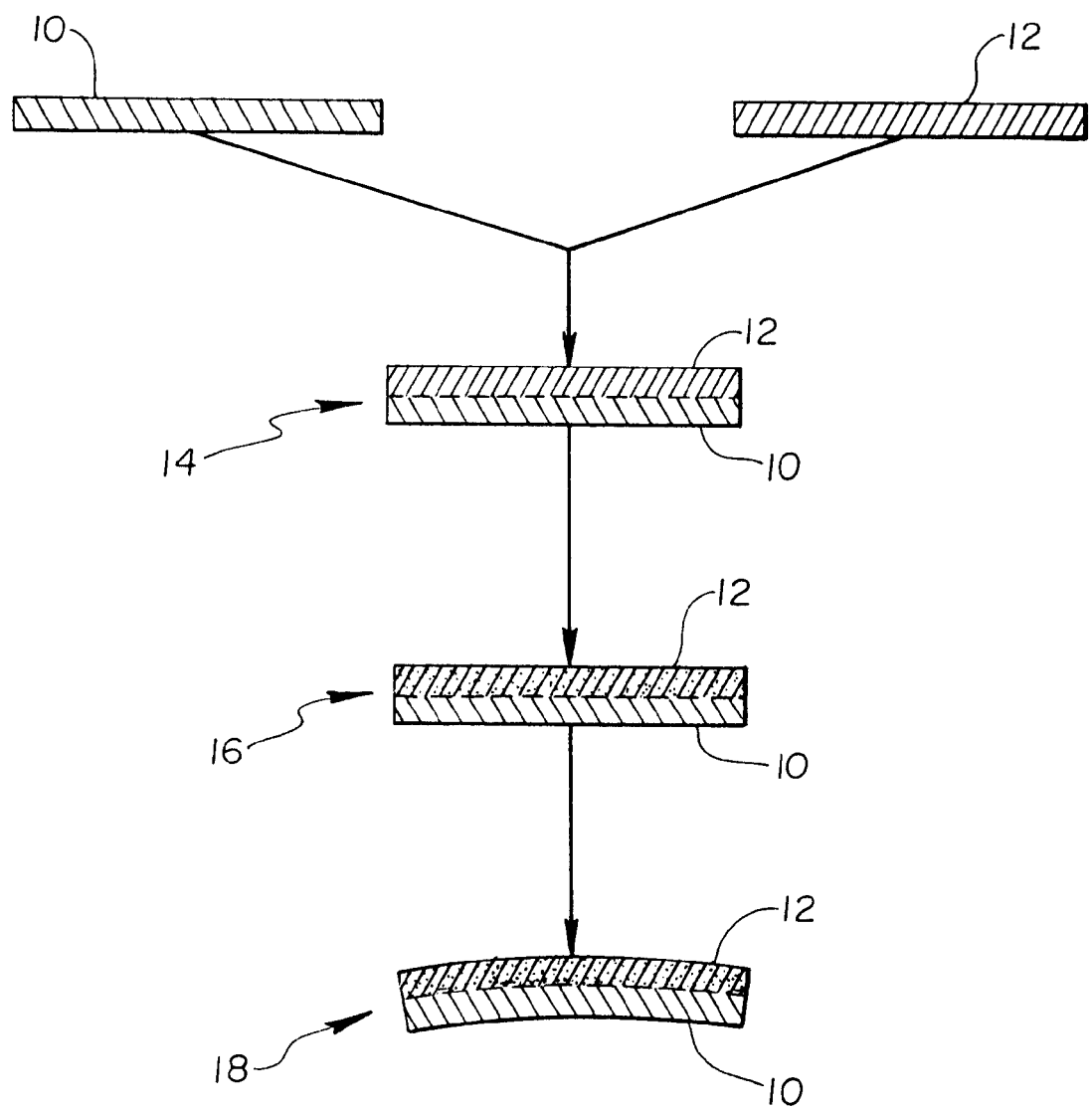
FIG. 1 is a schematic showing the fabrication and formation of one embodiment of a basic device making use of the general concept of the invention.

Referring now to FIG. 1, the present invention may comprise at least two layers of material, one being a non-water absorbable material 10, the other being a water absorbable material 12. The two layers may be combined by superimposing and joining them together as shown generally at 14 to provide a relatively two layer structure. When both layers are of polymeric material, which is most preferred, they may be combined together by the application of a suitable adhesive, heat or a solvent. When exposed to water, as shown at 16, and the water absorbing layer 12 swells upon absorbing water, deformation and/or bending occurs as seen at 18 due to the forces created in layer 12 upon swelling caused by the absorption of water.

To exhibit the requisite deformation and/or bending, it is only necessary that the two layers 10 and 12 exhibit different absorptive capacities. Both layers may be hydrophilic so long as one layer is more hydrophilic than the other. One layer may be non-absorptive and the other absorptive to maximize results. Both layers will preferably be polymeric in nature although the non-absorbing layer may even be thin metal.

The water absorptive layer may be of a material which is absorptive per se or, more preferably in certain applications described further hereinbelow, it may consist of any suitable polymeric material in a composite form including water-swellable particles of polymeric material as shown schematically in FIG. 1.

More than two layers may be utilized. These layers may be any combination of absorptive and non-absorptive or relatively less absorptive materials and may even include metallic and other non-polymeric layers depending on the strength desired and control over deformation which is desired or for other reasons.

Table 1 below lists examples of polymeric materials which may be used as layer 10 or as the matrix polymer material in a composite layer 12 for holding water-swellable particles.

TABLE 1

Biodegradable materials for the two-layer membrane include:

polylactic acid
polyglycolic acid
poly(lactide-co-glycolide)
poly(glycolide-co-trimethylene carbonate)
polydioxanone
polycaprolactone
poly(lactide-co-caprolactone)
poly(glycolide-caprolactone)
polyphosphate
polyanhydride
polyorthoester
poly(amino acid)
poly(hydroxyl butyrate)

Table 2 lists examples of polymeric materials which may be used as water swellable particles in a composite layer 12. All of those materials happen to be biodegradable as well. However, water swellable materials which are not biodegradable may be used.

TABLE 2 starch
gelatin
chitin
gum arabic
xanthan
cross-linked albumin
cross-linked hyaluronan
alginate Table 3 lists examples of water swellable polymeric material per se which may be used to form a water swellable layer 12 or in the alternative may be formed as particles and used in a composite layer 12 with another polymer material as the matrix. When layer 12 is in a composite form, even non-absorbent materials such as the polymeric materials of Table 1 may be used as the matrix material.

TABLE 3 collagen
cellulose derivatives
cross-linked poly(vinyl alcohol) and copolymers
cross-linked poly(vinylpirrolidone) and copolymers
poly(hydroxyethyl methacylate)
poly(ethylene glycol) and copolymers
polyacrylate
polyacrylate-co-starch
polyacrylate-co-polyacrylamide
polyacrylamide In Table 3, collagen and polyacrylate-co-starch are biodegradable. The rest are water soluble.

Other water swellable materials known in the prior art may be used in or for layer 12. For example, the hydrophilic polyurethanes and the like of U.S. Pat. No. 4,872,867; the water swellable plastic polymers of U.S. Pat. No. 5,163,952 its continuation U.S. Pat. No. 5,258,020 described in Examples 3, 7, 9, 10 and 11 and discussed in column 10 at lines 30–37 of those patents; the solid absorbents of U.S. Pat. No. 5,554,180 such as copolymers of cellulose and starch, agar and polymeric acids; the water swellable matrix materials of U.S. Pat. No. 4,460,642; the water swellable layers of U.S. Pat. Nos. 4,496,535 and 4,872,867 may be used.

Figure 2:
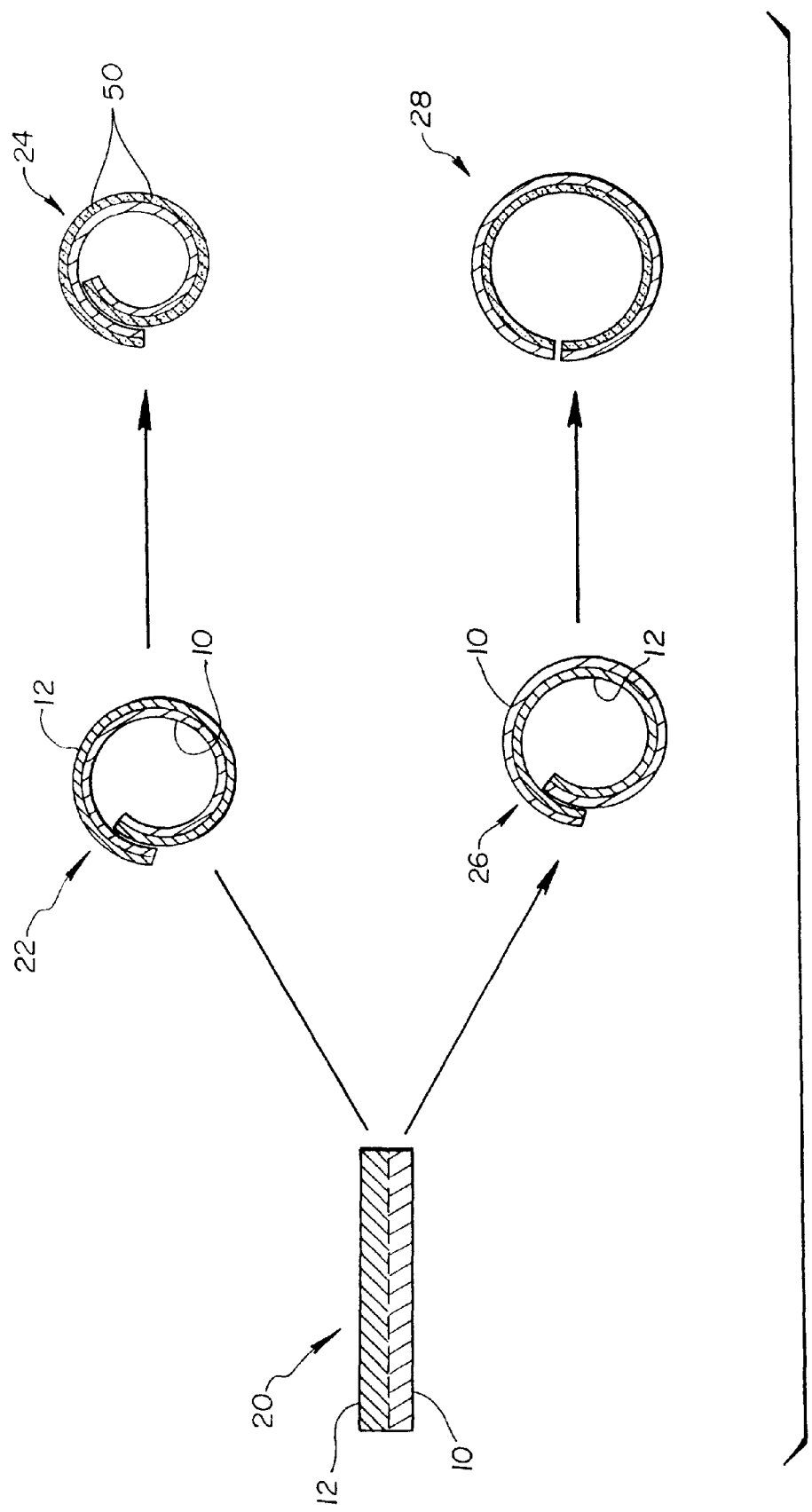
FIG. 2 is a schematic showing of two alternate embodiments of the invention which may be put to two distinctly different uses.
Figure 3:
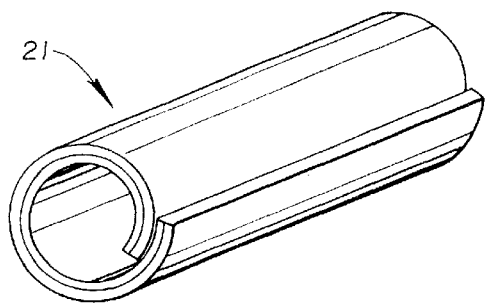
FIG. 3 is a showing of a configuration of a self-expanding stent in a normal size, making use of the invention.

Referring now to FIGS. 2 and 3, two preferred alternate embodiments of the invention will be described. If two elongated sheets 10 and 12 of polymeric material are superimposed together as shown at 20 in FIG. 2, and as already described with reference to FIG. 1, to form a two layer laminate like structure and the sheets are then rolled into an elongate tube 21 as shown in FIG. 3 in perspective view and in FIG. 2 in end view, in two alternate forms 22 and 24 as shown in FIG. 2, respectively, two different types of device are produced depending on which layer 10 or 12 is rolled on the inside of the tubular structure. If layer 12 is to the outside of the tube and layer 10 is to the inside as seen at 22 in FIG. 2, the tube will shrink in diameter as shown at 24 when layer 12 absorbs water or some other absorbent. If, on the other hand, layer 12 is to the inside of the tube and layer 10 is to the outside as shown at 26 in FIG. 2, the tube will expand in diameter as shown at 28 when layer 12 absorbs water or some other absorbent. Device 24 of FIG. 2 includes particles 50 of water swellable material.

The first type of device 22–24 of FIG. 2 may find use as a sealing device when placed around tubular conduits (not shown). In the presence of an absorbate, the device 22–24 will shrink around such a tubular conduit in a sealing relationship. For example, in a medical application such a device may be placed around a blood vessel or other body conduit which has been opened or otherwise requires patching and/or reinforcement on the exterior thereof. Such a device including a water absorbent will shrink by absorbing body fluids to tightly fit about the vessel or other body conduit. Of course, appropriate sizing relationships must be taken into account but these may be readily determined depending upon the particular materials selected and combined for the device, etc.

The presently most preferred embodiment of the invention involves the application of the concept to stent devices. The device 26–28 shown in FIG. 2 is such an embodiment and will function as a self-expanding stent for use on the inside of vessels and other body conduits. Again, consideration must be given to appropriate sizing for any given application of such a stent. However, such stents may be provided in any number of configurations and styles in addition to the configuration shown in FIGS. 2 and 3.

Figure 4:
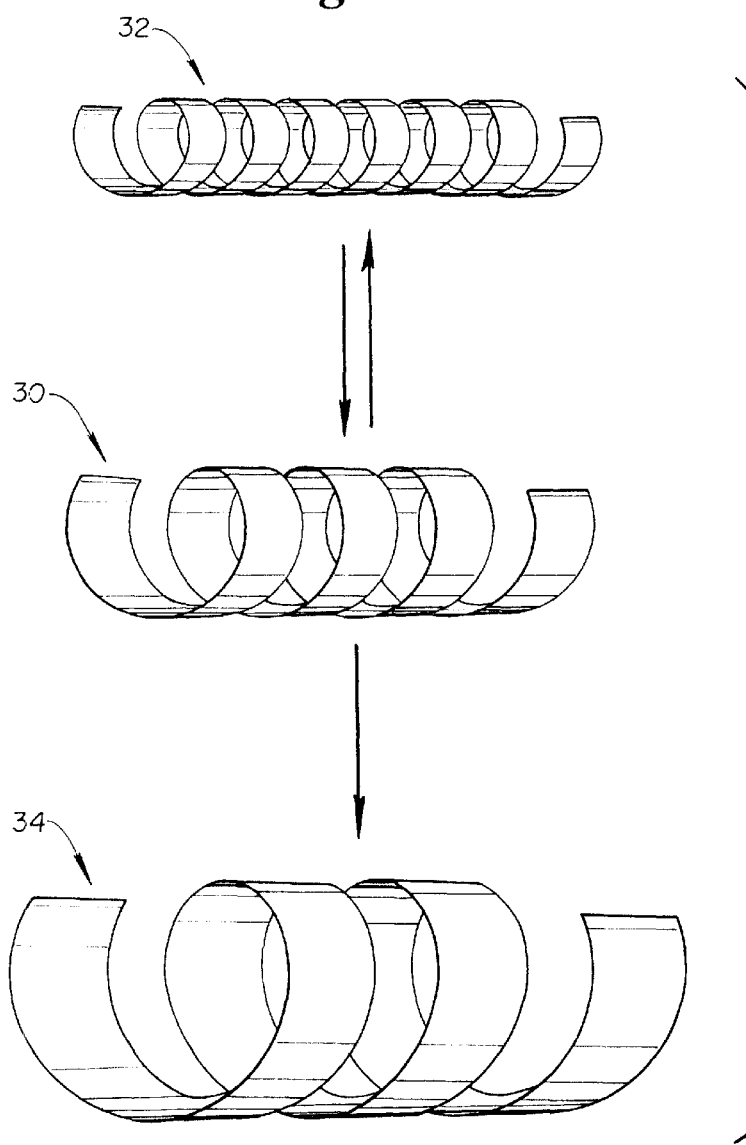
FIG. 4 is a schematic showing of the use of one of the embodiments of FIG. 2 as a self-expanding stent in a tubular/helical configuration loaded for deployment, in a deployed tubular/helical configuration and in an expanded tubular/helical configuration.

For example, a multi-layer structure according to the invention may be formed in a helical configuration of a normal predetermined size as shown generally at 30 in FIG. 4. Since this is a stent, the absorbent layer 12 will be positioned to the inside. The stent may be loaded onto a suitable catheter (not shown) for delivery as is known in the art. To minimize its diameter during delivery, it may be tightly wound to a smaller delivery diameter as shown at 32 when loaded onto the delivery catheter and covered with a removable sheath as is known in the art. Upon being positioned in the desired implantation location and exposed by removal of the sheath, stent 32 will first expand to its normal size 30 and will then, upon absorbing water in blood or other body fluid, self-expand to a predetermined enlarged and expanded size 34, the size depending on the inside diameter of the vessel in which it is to be used.

Figure 5:
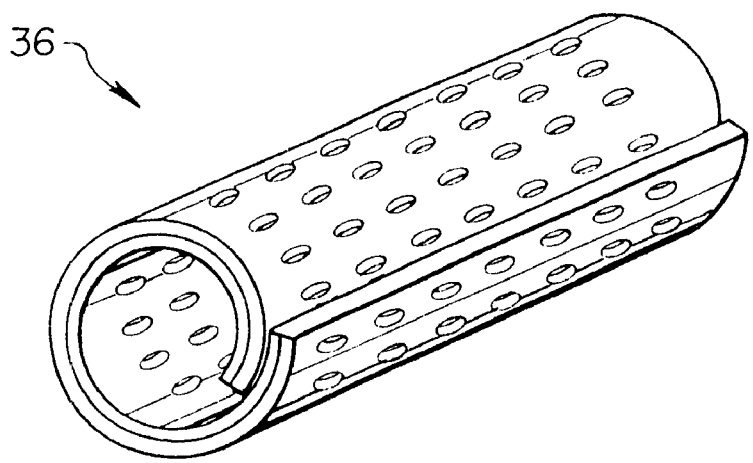
FIG. 5 is a showing of another stent embodiment.
Figure 6:
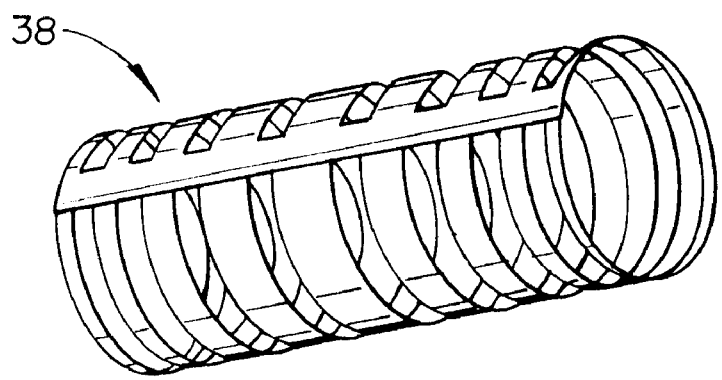
FIG. 6 is a showing of another stent embodiment.

Other configurations, not limited to rolled tubular configurations, may be used according to this invention for the two types of devices illustrated in FIG. 2. For example, a perforated tubular configuration 36 is shown in FIG. 5 and another configuration 38 is shown in FIG. 6. Many other configurations and structural types will be readily apparent to those familiar with the graft and stent art.

For medical applications of the concept of the invention, it may be desirable in certain instances such as stenting to make the device from all biodegradable materials. Such materials are included in Tables 1, 2 and 3 for example.

Although devices of more than two layers may make use of the concept of the invention, the detailed description herein is limited to two layer structures as they are presently most preferred.

EXAMPLES

Bilayer membranes, one hydrophobic and one hydrophilic, were prepared for demonstrating the application of the concept to stent usage. Hydrophobic layers of polycaprolactone (PCL) and layers of polydioxanone (PDS) were prepared by melting polymer on a hot plate and pressing it between two glass plates to form a membrane. Various thicknesses were prepared in this manner.

Hydrophilic (water swellable) layers were prepared in composite form, using gelatin particles in a polymer matrix of PCL or PDS. The gelatin was powdered in a mortar and separated by sieve to a 270 mesh size. The polymer was melted on a hot plate. The gelatin particles were mixed into it in 10% and 20% amounts. Then the melt was cast onto a warmed glass plate to form a membrane. Various thicknesses were prepared.

The membranes were superimposed together with tetrahydrofuran (THF) as a solvent adhesive or with heat used for adherence.

Gelatin absorbs water at room temperature (RT) or lower and expands in volume to become a gel without significant dissolution. At higher temperatures (about 70–100° C.) it will dissolve into water. In a stent application, with body temperature being about 37° C., gelatin will absorb water and not dissolve appreciably.

As can be seen from the above discussion, the two layers may make use FIG. 6c is a magnified view of the circled region 6c of FIG. 6a; of the same polymer when a composite layer form is utilized. However, different polymers for the two layers may also be used. Also, the non-absorbing layer may be metallic in thin film form or in other forms. As already noted, biodegradable or non-biodegradable materials may be used. The layers may be superimposed together with adhesive or by means of heat melting. One layer can be placed on the other layer as a coating.

The expansion force of a bilayer formed as a coil or cylinder can be controlled by the thickness of the layers, the loading amount of water absorbent material included in a composite type layer, the capability or capacity of the particular material for water absorbance and its expanding volume, and the type of polymer and its molecular weight.

Specific examples are comprised of a PCL layer superimposed on a PCL and gelatin composite layer. Several PCL membranes were formed in various thicknesses.
(1) 0.06–0.07 mm.
(2) 0.09–0.10 mm.
(3) 0.12–0.13 mm.
(4) 0.13–0.14 mm.
(5) 0.17–0.18 mm.
(6) 0.30–0.31 mm.
These membranes were formed by heating and melting the polymer in a glass vial on a hot plate at a temperature of about 70–80° C. The melt was placed on a flat glass plate. The thickness of the resultant membrane is dependent on the amount of melt placed on the plate and the pressure used in pressing it. A second glass plate is placed on top of the melt and the two plates are pressed together. The plates are warmed during this procedure. After the membrane has a smooth appearance and thickness the top plate is removed and the membrane is allowed to cool. The membrane is then peeled off of the remaining plate and cut to size, for example 8.0 mm. width strips.

PCL and gelatin composite layers were also formed in various thicknesses and gelatin loading.

10% by weight gelatin powder (particle size 270 mesh)
(1) 0.09–0.10 mm.
(2) 0.13–0.14 mm.
(3) 0.18–0.20 mm.
(4) 0.21–0.22 mm.
(5) 0.25–0.26 mm.
(6) 0.31–0.32 mm.

20% by weight gelatin powder (270 mesh)
(1) 0.07–0.08 mm.
(2) 0.09–0.12 mm.
(3) 0.13–0.14 mm.
(4) 0.21–0.22 mm.
(5) 0.25–0.26 mm.

These membranes were formed by heating and melting the PCL polymer in a vial on a hot plate at about 100° C. The gelatin was mixed into the melt and a quantity of the melt (the amount depending on desired thickness) was transferred to a warm glass plate. A second glass plate was placed on the melt and the plates were pressed together while heating them. After achieving a smooth appearance the top plate was removed and the membrane was allowed to cool on the bottom plate after which it was peeled off and cut to size, for example 0.9 mm. width strips.

Several rolled cylinder samples were made by superimposing various of the membranes together. For example, a 10% gelatin and PCL membrane of 0.13 mm. thickness was combined with a PCL membrane of 0.10 mm. thickness. A 20% gelatin and PCL membrane of 0.13 mm. thickness was combined with a PCL membrane of 0.10 mm. thickness.

The two layers were combined by using a 1% PCL solution in THF as adhesive which was coated on one side of each membrane. They were then placed together and held for one hour.

A heat gun was used to warm the bilayer which was then rolled to form a closed cylinder having the configuration shown in FIG. 3. Two interfitting glass tubes can be used to facilitate this procedure.

When these cylinders were dropped into water at room temperature, expansion was observable within five minutes. Full expansion was observed overnight with the 20% gelatin samples exhibiting greater expansion than the 10% samples. This demonstrates that the amount of expansion is dependent on the level of gelatin loading.

Utilizing the following code, additional examples of stents were prepared as above described.
PCL membrane, 9.0 mm. wide strips
D1 0.06–0.07 mm. thick
D2 0.09–0.10 mm. thick
Composite membrane 10% gelatin and PCL, 9.0 mm. wide strips
X1 0.09–0.10 mm. thick
X2 0.13–0.14 mm. thick
Composite membrane 20% gelatin and PCL, 9.0 mm. wide strips
Y2 0.13–0.14 mm. thick
Y5 0.25–0.26 mm. thick
The various combinations of these membranes are identified as follows:

$$D2+X2=DX22$$

$$D2+YS=DY22$$

$$D1+Y2=DY12$$

When formed into rolled cylinders, the following expansion results were observed in water at room temperature:

| Sample | Test Time (Opening in m.m.) | | | | | |
|--------|------|------|------|------|--------|--------|
|        | 1 hr. | 2 hr. | 4 hr. | 1 day | 2 days | 5 days |
| DY12   | 9.77 | 11.16 | 11.65 | 11.25 | 11.93 | 11.54 |
|        | 7.03 | 8.81 | 8.96 | 9.01 | 9.41 | 9.10 |
| DY22   | 4.99 | 7.68 | 8.40 | 8.61 | 9.19 | 9.44 |
|        | 3.59 | 5.09 | 6.68 | 6.81 | 7.68 | 7.43 |
| DY15   | 3.55 | 6.97 | 7.84 | 8.45 | 9.05 | 9.09 |
|        | 4.72 | 5.88 | 8.94 | 9.80 | 9.77 | 9.58 |
| DY25   | 3.12 | 4.94 | 6.35 | 6.95 | 7.63 |      |
|        | 4.81 | 6.48 | 8.17 | 9.67 | 9.81 | 9.99 |
| DX22   | 3.28 | 4.20 | 4.29 | 4.35 | 4.40 | 4.54 |
|        | 3.13 | 3.84 | 4.39 | 4.44 | 4.47 | 4.57 |

Stents having the configuration shown in FIG. 4 were made utilizing bilayer membranes 1.0 mm. wide and 44–55 mm. long of DY23 combination. The strips were helically wound around a glass tube and oven heated at 52–57° C. for 15 minutes. After cooling the stent held the glass tube size and a fixed tubular/helical shape.

Utilizing biodegradable polydioxanone (PDS), melting temperature 104.7° C., as the polymer, several bilayers were prepared.

The polymer was melted and divided into two portions. One portion was cast to provide membranes of 0.09–0.10 mm. thick. One portion was loaded with 20% gelatin filler and cast to provide membranes 0.13–0.14 mm. thick. Bilayers were formed by bonding the membranes together by heating them almost to melting or by pre-loading with PCL/THF and heating almost to melting.

The resultant bilayer was formed into a tubular/helical shape by cutting the membrane into 1.8 mm. wide strips and wrapping them onto 3.0–4.0 mm. diameter glass tubes which were inserted into larger tubes. These molds were placed in a 95° C. oven for 15 minutes then cooled. These stents when placed in water expanded from 4.0 mm. to 5.6 mm. (OD).

All of the stents described above provided a strong holding force believed to be appropriate for stent function.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A multilayer polymeric device in the form of a stent comprised of at least two superimposed layers formed into a generally cylindrical shape, one layer being liquid swellable, the other being less so, and wherein the liquid swellable layer forms an outer layer of the device, the device shrinking in response to liquid absorption.

2. The device of claim 1 wherein the liquid swellable layer and the other layer are formed of biodegradable polymeric material.

3. A multilayer polymeric device comprised of at least two superimposed layers formed into a generally cylindrical shape, one layer being liquid swellable, the other being less so, the liquid swellable layer and the other layer formed of the same polymeric composition and the liquid swellable layer including particles of water swellable material, the liquid swellable layer forming an outer layer of the device, the device shrinking in response to liquid absorption.

4. The device of claim 1 wherein the liquid swellable layer is water absorbable.

5. The polymeric device of claim form 1 in the form of a sleeve.

6. The device of claim 1 in the form of a rolled up sheet.

7. The device of claim 1 in the form of a closed cylinder.

8. The device of claim 1 wherein the other layer is metallic.

9. The device of claim 1 wherein the other layer is a vapor deposited layer on the one layer.

10. The device of claim 1 in which one of the layers carries a drug to be released.

11. The multilayer polymeric device of claim 1 in the form of a sleeve configured for implantation in the body wherein the sleeve shrinks in response to liquid absorption.

12. The multilayer polymeric device of claim 11 wherein the other layer forms an innermost layer of the sleeve.

13. The multilayer polymeric device of claim 11 wherein the one layer is polymeric and the other layer is polymeric.

14. The multilayer polymeric device of claim 11 including a metallic layer.

15. The multilayer polymeric device of claim 11 wherein the one layer is water swellable and the other layer is less water swellable than the other layer.

16. The multilayer polymeric device of claim 1 in the form of a tube configured for implantation in the body, the tube having an outer diameter and inner diameter, the superimposed layers arranged such that the inner diameter of the tube changes in response to liquid absorption.

* * * * *